United States Patent [19]

Hickam et al.

[11] 4,357,576
[45] Nov. 2, 1982

[54] CONDUCTIVITY CELL

[75] Inventors: William M. Hickam, Churchill; Pang-Kai Lee, Murrysville; William T. Lindsay, Jr., Hempfield Township, Westmoreland County, all of Pa.

[73] Assignee: Westinghouse Electric Corp., Pittsburgh, Pa.

[21] Appl. No.: 197,317

[22] Filed: Oct. 15, 1980

[51] Int. Cl.³ .................................................. G01N 27/42
[52] U.S. Cl. ........................................ 324/450; 324/449
[58] Field of Search ...................... 324/446, 448–450, 324/441, 439

[56] References Cited

U.S. PATENT DOCUMENTS 3,161,823  12/1964  Uithoven ............................ 324/448
3,302,102  1/1967  Lace .................................... 324/449
3,373,351  3/1968  Rak ..................................... 324/449
3,919,627  11/1975  Allen ................................... 324/448

Primary Examiner—Michael J. Tokar
Attorney, Agent, or Firm—D. Schron

[57] ABSTRACT

A conductivity cell wherein thin film or foil electrodes are supported in a case or holder and are separated by an electrically insulative spacer member. A small portion of each electrode together with an exposed surface of the spacer member forms a channel in which thin films of an electrolyte may be deposited from a measured environment and with the electrodes being connected to a conductivity circuit the conductance of the thin film may be measured. If the electrolyte and its concentration are known, the film thickness and deposition rate in the channel may be obtained.

9 Claims, 12 Drawing Figures

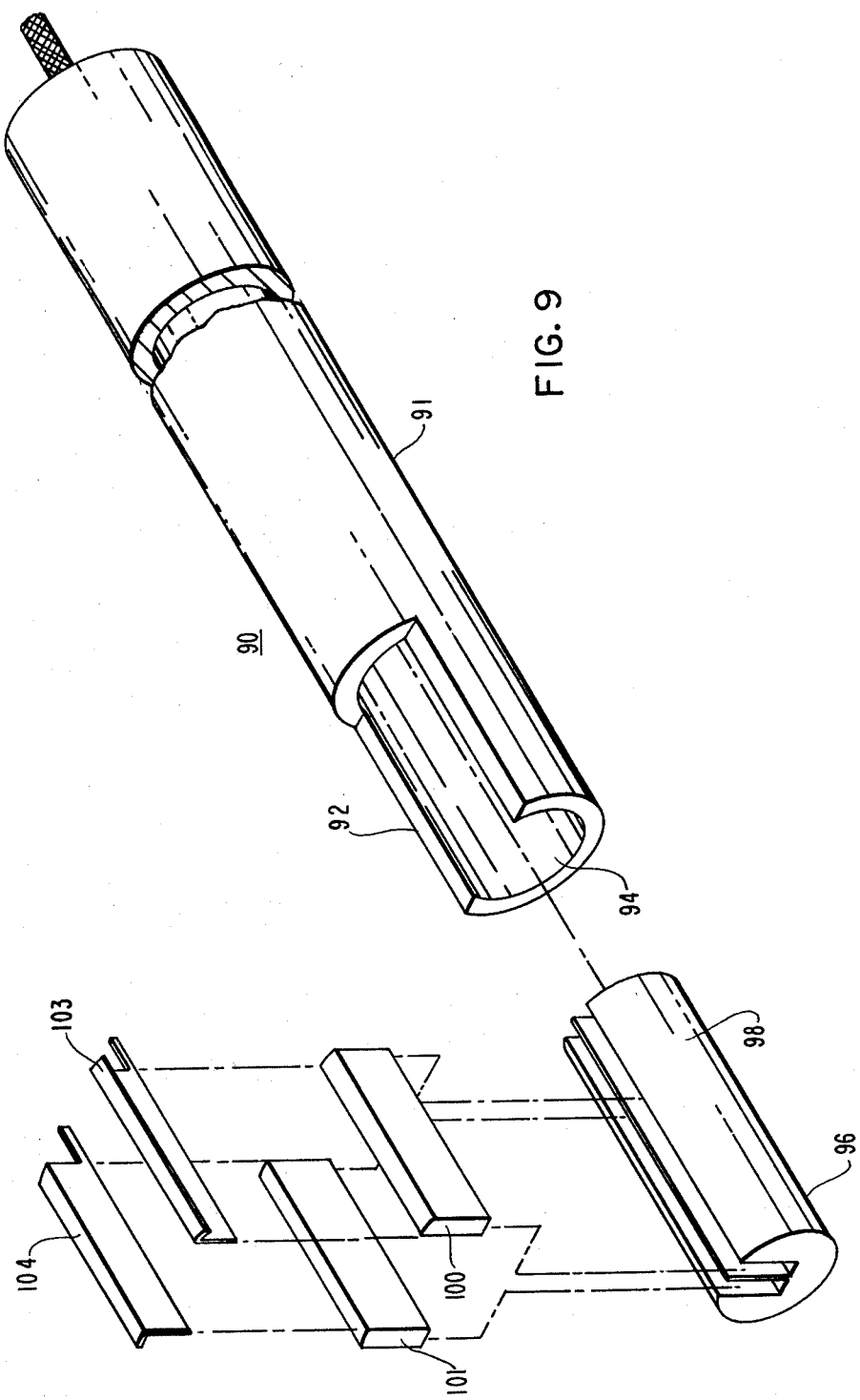

CONDUCTIVITY CELL

CROSS-REFERENCE TO RELATED APPLICATIONS

The present invention is related to application Ser. No. 197,378, filed Oct. 15, 1980.

BACKGROUND OF THE INVENTION

1. Field of the Invention

The invention in general relates to conductivity cells and more particularly to a rugged cell for use in a hostile environment.

2. Description of the Prior Art

Conductivity cells for measuring the electrical conductivity of a fluid generally are comprised of two separated plates forming electrodes to which an electric potential is applied. By connecting the electrodes to a measuring circuit or device (such as a conductivity bridge or conductivity meter), the electrical conductance of a fluid introduced between the electrodes may be obtained.

Such structures are not conducive for use in a hostile environment. For example, as described in the aforementioned copending application in a steam turbine system, superheated steam often contains low concentrations of various impurities, one of which is sodium chloride. During the steam cycle operation, and due to the expansion of the steam in the low pressure section of the turbine it is possible that the entrained sodium chloride could form a saturated solution which if deposited upon the turbine rotor blades can lead to corrosion and cracking.

Conductivity sensors of the prior art are not adapted to measure conductivity in the hostile environment of an operational steam turbine. Further, the sodium chloride solution is deposited in the form of a thin film, the conductance of which cannot be measured by the spaced apart electrodes of the prior art conductivity cells.

SUMMARY OF THE INVENTION

The conductivity cell of the present invention is adapted for use in hostile environments such as an operational steam turbine and is adapted to provide an indication of the buildup of thin films of corrosive deposits such as sodium chloride or other salts or hydroxides which are strong electrolytes.

The conductivity cell of the present invention includes first and second spaced apart electrodes to which may be connected an electrical potential. An electrically insulative spacer member is interposed between, and contacts both electrodes and includes a surface portion which extends between the electrodes and is exposed such that a thin film of electrolyte may be deposited thereon. The cell may be connected in any one of a number of well-known conductivity measuring circuits and a measurable electric current is established between the electrodes through the electrolyte deposition on the surface portion of the spacer between the electrodes so as to provide an indication of such deposition and therefore the presence of the electrolyte in the measured environment.

BRIEF DESCRIPTION OF THE DRAWINGS

FIG. 9 is an exploded view of yet another probe embodiment; and

DESCRIPTION OF THE PREFERRED EMBODIMENTS

Figure 1:
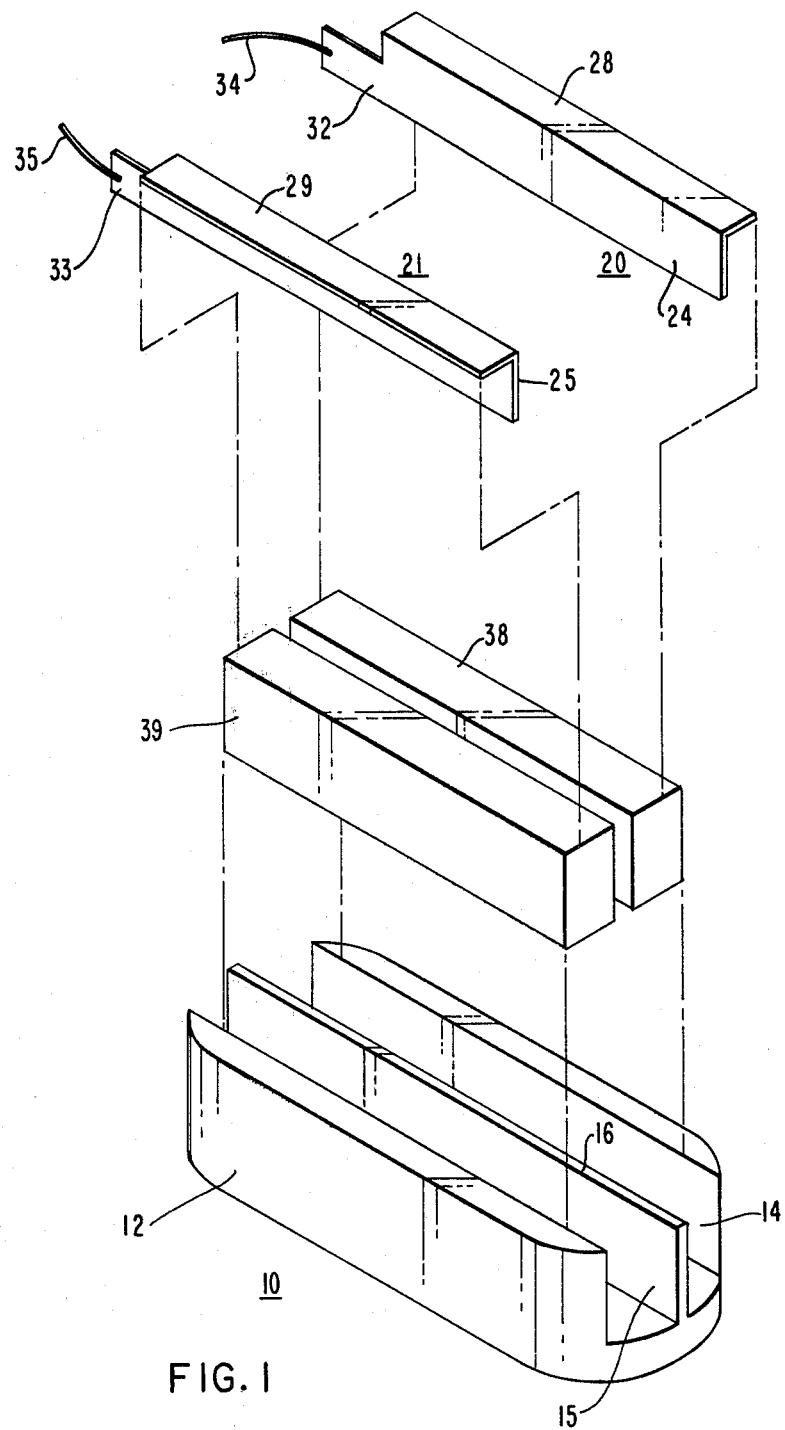
FIG. 1 is an exploded view and FIG. 1A is a perspective view of a conductivity cell in accordance with one embodiment of the invention.
Figure 1A:
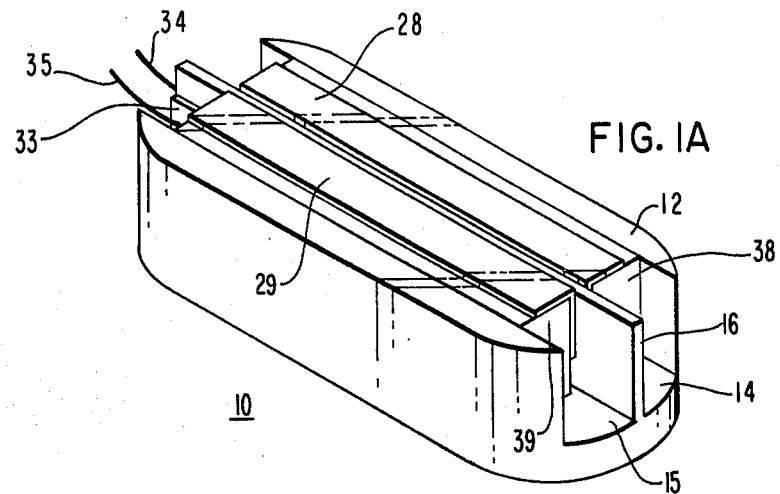
Figure 2:
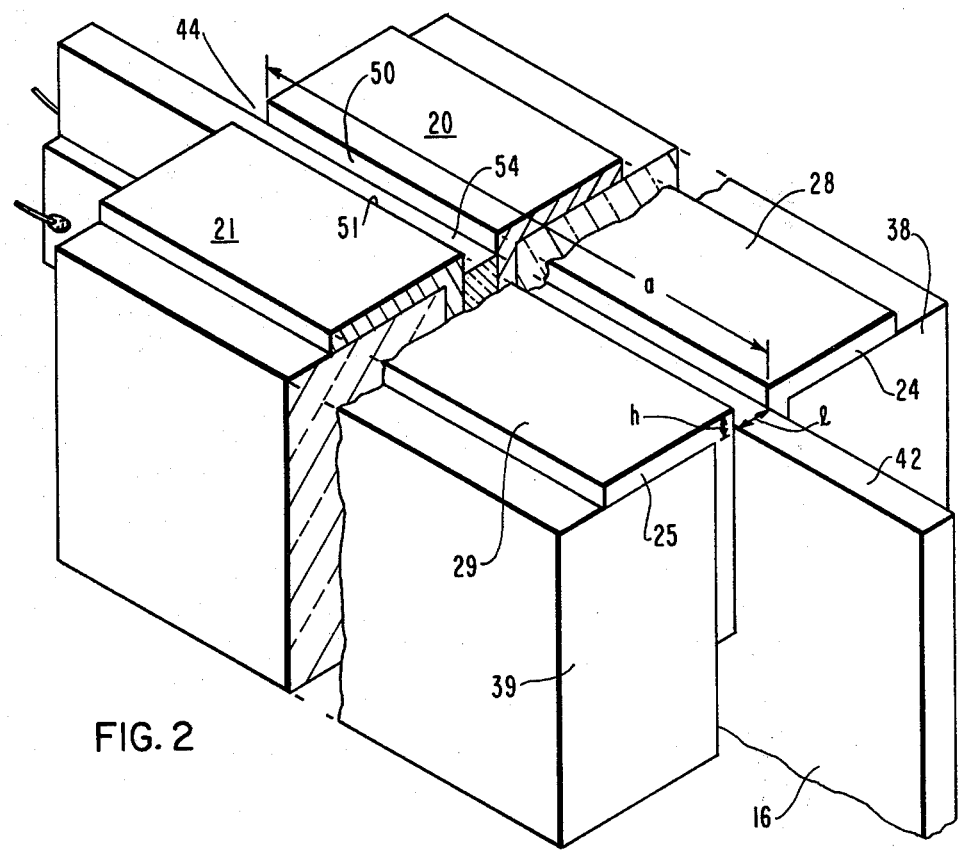
FIG. 2 is a perspective view of a portion of the conductivity cell of FIG. 1A.

FIGS. 1 and 2 illustrate a typical conductivity cell in accordance with one embodiment of the present invention. The conductivity cell 10 includes a holder 12 which may have machined therein slots or grooves 14 and 15 separated by a partition or spacer member 16. Holder 12 together with spacer member 16 is fabricated from electrically insulating material, and if subject to hostile environments, a typical material might be a glass-ceramic such as that put out by the Corning Glass Works under their trade name of Macor.

The conductivity cell further includes first and second electrodes 20 and 21 fabricated from metal foil such as platinum and folded into the shape illustrated in FIG. 1 so as to include respective wall portions 24 and 25 as well as respective top portions 28 and 29. Extension tabs 32 and 33 are provided so as to accommodate, for example by spot welding, respective electrical leads 34 and 35.

Electrodes 20 and 21 are placed upon respective electrode supports 38 and 39 which are in turn placed into respective slots 14 and 15 of holder 12. The conductivity cell components are assembled and held together by means of a high temperature adhesive such as Epoxylite 810 of the Epoxylite Corporation.

FIG. 2 is an enlarged view illustrating the relationship between the spacer member 16 and electrodes 20 and 21. It is seen that surface 42 of spacer member 16 extends between and contacts electrodes 20 and 21 and together with the exposed areas 50 and 51 of electrode wall portions 24 and 25 forms a channel 54 which can accommodate the deposition of thin film electrolytes. The exposed upper sections 50 and 51 of wall portions 24 and 25 are separated by a distance l and are each of a height h above the surface 42, where h would be equivalent to the foil thickness of the respective electrodes 20 and 21, each of a length a.

In operation, the electrodes are connected to a conductivity bridge or meter and the cell is placed in an environment wherein deposition of a thin film of an electrolyte onto surface 42 may occur. The electric current from one electrode to the other is modulated by the electrolyte such that the presence of an electrolyte may be detected as well as its deposition rate within the channel 44. If only one type of electrolytic deposition takes place and the physical constants of the electrolyte are known, then, knowing the cell dimensions l, h and a the thickness of the deposited electrolyte may be determined as well as its rate of buildup, mass, and mass buildup per area per unit of time.

Figure 3:
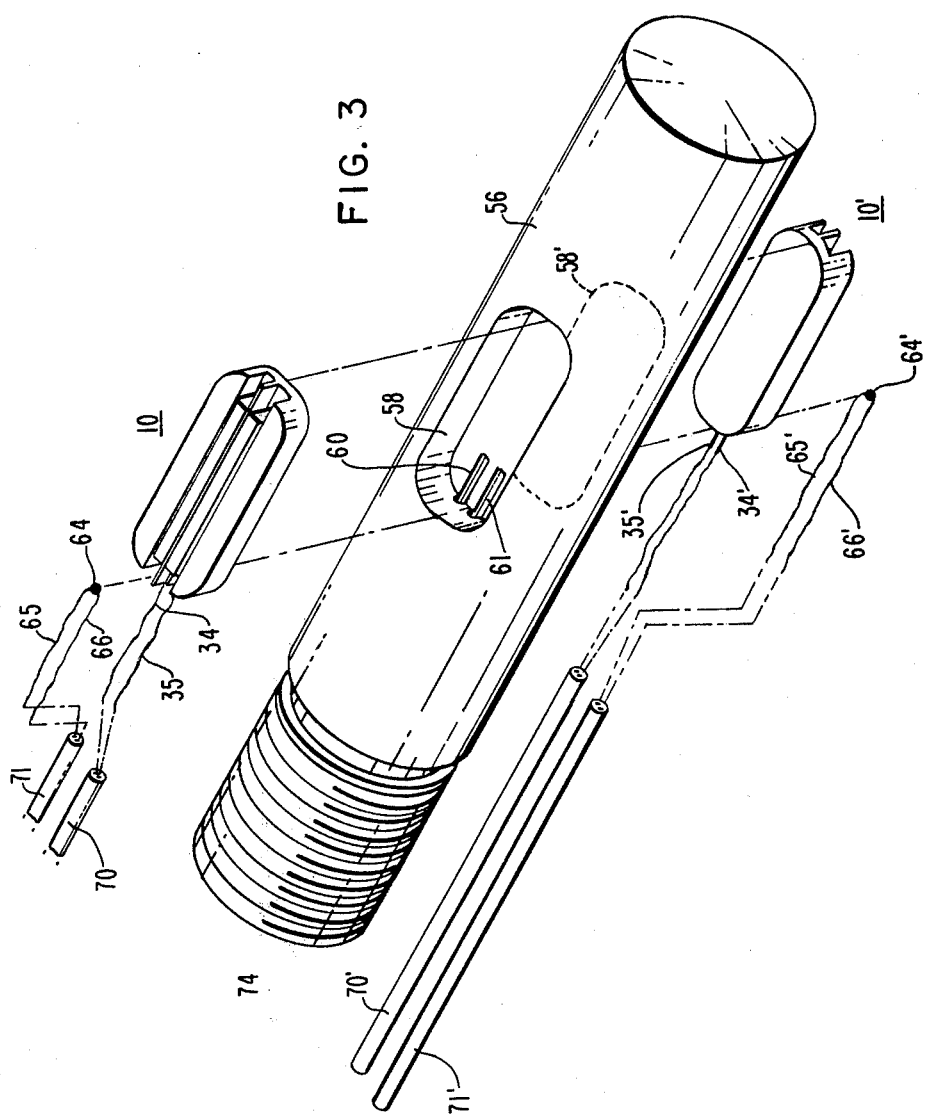
FIG. 3 is an exploded view of a probe utilizing the conductivity cell of FIG. 2.
Figure 4:
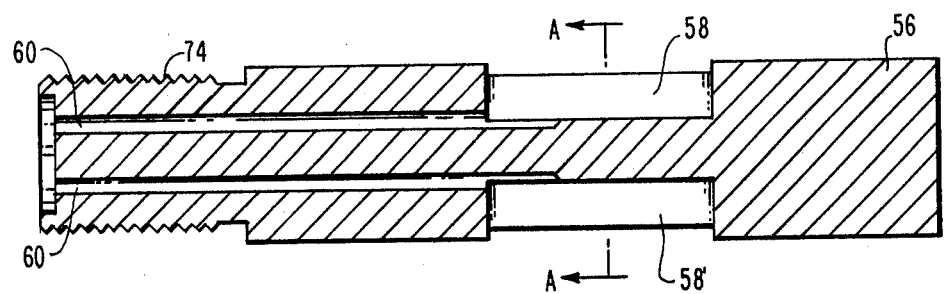
FIG. 4 is a sectional view of the probe of FIG. 3.
Figure 5:
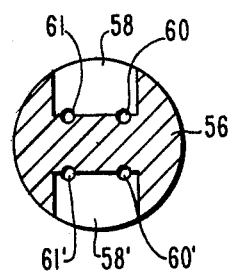
FIG. 5 is a sectional view along line A—A of FIG. 4.

When utilized in a hostile environment it may be desirable to provide a carrier or housing for the conductivity cell, as illustrated in FIG. 3. FIG. 4 additionally shows an axial cross-sectional view through the housing and FIG. 5 is a view along line A—A of FIG. 4.

The housing 56, which may be fabricated from stainless steel rod, includes a cavity 58 for the reception of conductivity cell 10. If desired, a second cavity 58' may be provided to accommodate for a second or backup cell 10'.

Apertures 60, 61 and 60', 61' may be drilled into the housing 56 from the rear thereof to respective cavities 58 and 58' to accommodate various sensor leads.

In use, it may be desirable to obtain, in addition to a conductivity reading, a temperature reading of the environment being measured. For this purpose a temperature sensor in the form of a thermocouple 64 may be provided and placed in one of the slots of the conductivity cell 10 to provide an output signal on leads 65 and 66 indicative of temperature. A corresponding temperature sensor 64' may be provided for conductivity cell 10'.

Ceramic rods 70 and 71 (and counterpart rods 70' and 71') are provided with each including two longitudinal apertures therethrough such that the apertures in rod 70 can respectively accommodate leads 34 and 35 of conductivity cell 10 and the apertures in rod 71 can respectively receive leads 65 and 66 of thermocouple 64. Rods 70 and 71 in turn may be placed in respective apertures 60 and 61 of housing 56 with the wires extending from the rear housing then being connectable with electronic measuring equipment. The conductivity cells 10 and 10' with the thermocouple 64 and 64' may be maintained in the respective cavities 58 and 58' by means of the aforementioned Epoxylite 810 adhesive.

Figure 6:
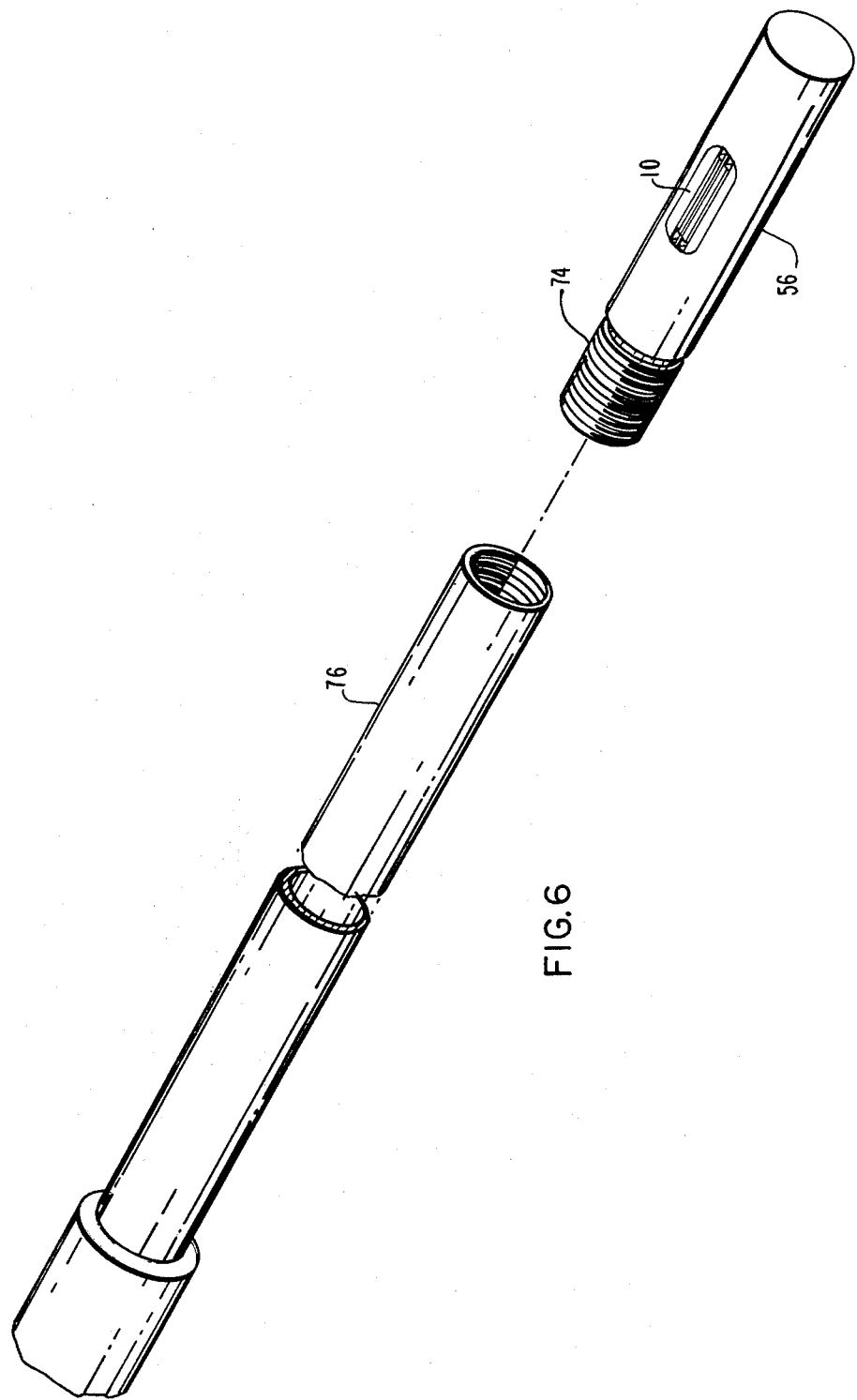
FIG. 6 illustrates the probe of FIG. 3 together with an extension handle.

The housing 56 together with the respective conductivity cells forms a probe which may be placed in a hostile environment. In some systems, such as in a turbine system, it may be necessary to support the probe at some distance from the measuring point. Accordingly, the rear portion of housing 56 is threaded at 74 so as to connect with an elongated handle member 76, as illustrated in FIG. 6.

Figure 8:
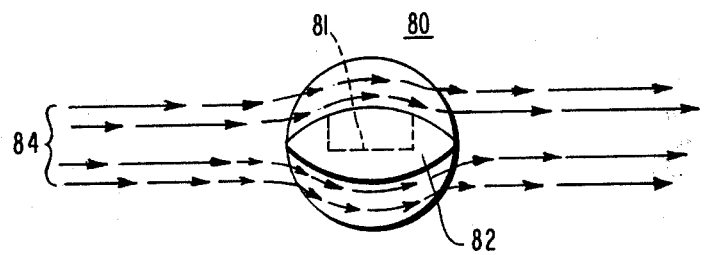
FIG. 8 is an end view of the probe of FIG. 7.
Figure 7:
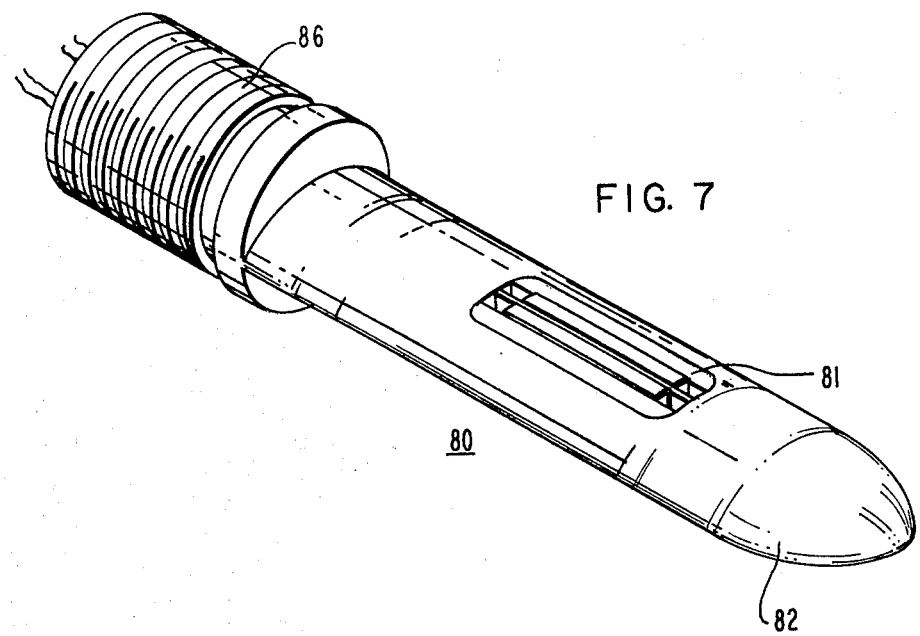
FIG. 7 is a view of another type of probe in conjunction with the conductivity cell of FIG. 2.

FIG. 7 illustrates another probe 80 having a cavity for receipt of a conductivity cell 81. The probe housing 82, as further illustrated in the end view of FIG. 8, has a streamlined or aerodynamic shape so that the probe may be placed into a flowing environment, as represented by flow lines 84, and by virtue of the streamlined shape will not impede flow conditions nor the conditions under which condensation of an electrolyte may occur. Probe 80, in a manner similar to that illustrated in FIG. 6, includes a threaded end section 86 for connection to a handle or other support member (not illustrated).

FIG. 9 illustrates a probe 90 having a cylindrical housing 91 with an open end 92 for receipt of a conductivity cell. A cylindrical cavity 94 accommodates a conductivity cell 96 having components similar to that illustrated in FIG. 1 but with the holder 98 thereof having a cylindrical shape so as to be accommodated in the cylindrical cavity 94. The electrode supports 100 and 101 for electrodes 103 and 104 may each be machined to have a curved upper surface so as to conform generally to the cylindrical shape of holder 98. In this regard the holders and electrode supports of conductivity cells 81, and 10 and 10' may be shaped so as to conform to the outer surface of the probe housings in which they are respectively located. Although not illustrated in FIGS. 7 and 9 a thermocouple may be included in the arrangement for temperature measurements as was the case with respect to FIG. 3.

Figure 10:
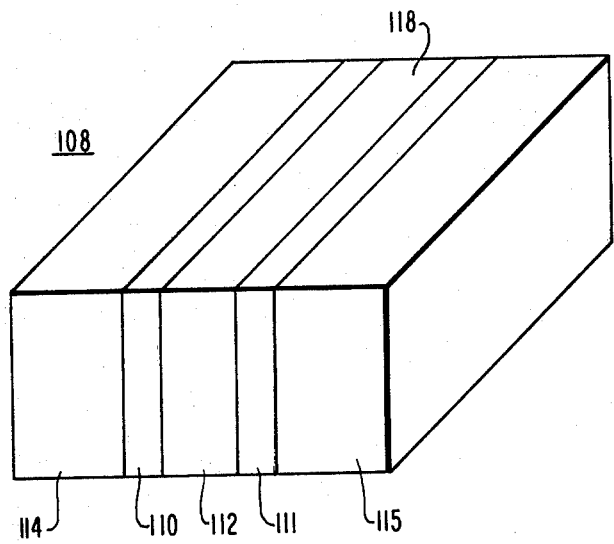
FIGS. 10 and 11 illustrate alternate conductivity cell constructions.

FIG. 10 illustrates a conductivity cell 108 which includes first and second electrodes 110 and 111 with an electrically insulative spacer member 112 therebetween. Members 114 and 115 may be provided to add additional support for the electrodes. The upper surface 118 of spacer member 112 forms a surface susceptible to deposition of thin films of electrolyte.

Figure 11:
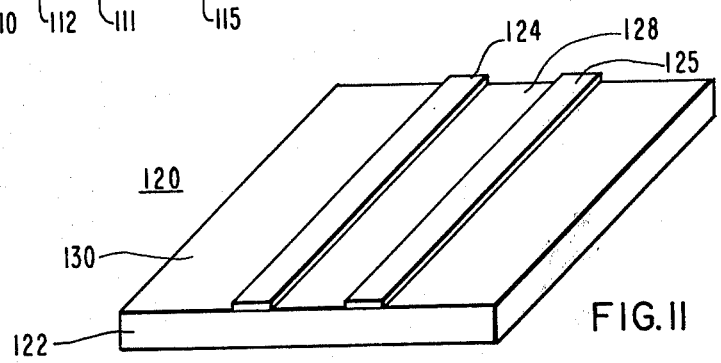

Another conductivity cell 120 is illustrated in FIG. 11 wherein the electrically insulative member 122 forms the support and the spacer for electrodes 124 and 125 which may be deposited on, or otherwise affixed to member 122. Surface portion 128 of member 122 is disposed between electrodes 124 and 125 and is subject to electrolyte deposition in a measured environment and with the arrangement of FIG. 11, thicknesses and deposition rates within channel 130 may be obtained, as was the case with the structure of FIG. 1.

Although the invention has been described with respect to conductance measurements of extremely thin films such as may be encountered in a steam turbine system, it is to be understood that the cell is equally adaptable for measurement in other environments as well as the conductance measurements of liquids.

What is claimed is:

1. A conductivity cell for use in an environment which may include the deposition of thin films of an electrolyte, comprising:
   (A) an elongated holder having first and second elongated slots separated by a spacer member having a top surface portion susceptible to deposition of thin films of electrolyte;
   (B) first and second foil electrodes;
   (C) first and second electrode supports for respective support of said first and second electrodes;
   (D) said first and second supports being positioned within respective ones of said first and second slots;
   (E) said first and second electrodes being supported so as to extend beyond said top surface portion of said spacer member thereby forming a channel therewith, for said electrolyte deposition therein.

2. Apparatus according to claim 1 wherein:
   (A) said first and second electrodes are folded over their respective supports so as to extend beyond said top surface portion by a distance equivalent to the thickness of said foil.

3. Apparatus according to claim 1 wherein:
   (A) said electrode each includes a tab portion which extends past said support for connection of an electrical lead.

4. Apparatus according to claim 1 which includes:
   (A) a housing member having a cavity therein,
   (B) said conductivity cell being positioned within said cavity.

5. Apparatus according to claim 4 wherein:
   (A) said housing member includes two said cavities;
   (B) two of said conductivity cells being positioned within respective cavities.

6. Apparatus according to claim 4 which includes:
   (A) a thermocouple positioned within said cavity.

7. Apparatus according to claim 4 wherein:

(A) said housing member is cylindrical.

8. Apparatus according to claim 4 wherein:

(A) said housing member has a streamlined aerodynamic shape for placement in a flowing environment.

9. Apparatus according to claim 4 which includes:

(A) an elongated handle member connected to said housing member.

* * * * *